United States Patent [19]

Corriu et al.

[11] Patent Number: 4,841,084
[45] Date of Patent: Jun. 20, 1989

[54] NEW HEXACOORDINATE SILICON COMPLEXES, THE PROCESS FOR THEIR PREPARATION AND THEIR APPLICATION

[75] Inventors: Robert J. Corriu; Geneviève E. Cerveau, both of Montpellier; Claude G. Chuit, Palavas les Flots; Catherine Reye, Montpellier, all of France

[73] Assignee: Centre National de la Recherche Scientifique, Paris, France

[21] Appl. No.: 813,128

[22] Filed: Dec. 24, 1985

[30] Foreign Application Priority Data

Dec. 27, 1984 [FR] France ................. 84 19886

[51] Int. Cl.⁴ .......................... C07F 7/08; C07F 7/18
[52] U.S. Cl. .................... 556/464; 556/406; 556/430; 556/449; 556/466; 556/478; 556/487; 556/489
[58] Field of Search ............ 556/464, 466, 478, 449, 556/487, 489, 430, 406

[56] References Cited

U.S. PATENT DOCUMENTS 3,355,477 11/1967 Frye ....................... 556/465

OTHER PUBLICATIONS

Rosenheim et al., "Z. Anorg. Chem.", 196, pp. 160–162 (1931).
Barnum, "Inorg. Chem.", 11, pp. 1424–1429 (1972).
Barnum et al., "Inorg. Chem.", 12, pp. 497–498 (1973).

*Primary Examiner*—Paul F. Shaver
*Attorney, Agent, or Firm*—Fulbright & Jaworski

[57] ABSTRACT

The present invention relates to new hexacoordinate silicon complexes, the process for their preparation and their application.

These new complexes correspond to the general formula I:

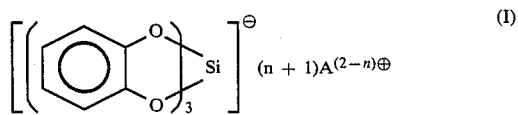

in which:
A represents an alkali metal or alkaline earth metal except for magnesium, and
n=0 or 1.

20 Claims, No Drawings

NEW HEXACOORDINATE SILICON COMPLEXES, THE PROCESS FOR THEIR PREPARATION AND THEIR APPLICATION

The present invention relates to new hexacoordinate silicon complexes, the process for their preparation and their application.

The hexacoordinate silicon complexes according to the invention correspond to the general formula I;

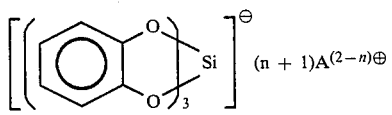

in which:
A represents an alkali metal or alkaline earth metal except for magnesium, and
n=0 or 1.

According to the present invention, these complexes can advantageously be prepared by reacting silica or inorganic or organic silicates with pyrocatechol in the presence of a base.

An example of inorganic starting silicates which may be mentioned is calcium hexafluorosilicate and examples of organic silicates which may be mentioned are the silicates of the formula Si(OR)$_4$, in which R represents an alkyl radical containing from 1 to 6 carbon atoms. These organic silicates can be prepared by conventional processes described, for example, in "Chemistry and Technology of Silicones" (W. Noll).

An alkali metal alcoholate or alkaline earth metal alcoholate, for example sodium methylate, may advantageously be used as the base necessary for carrying out the above process, it being possible in particular for the said alcoholate to be prepared in situ in the reaction medium.

In general, the reaction of the silica or the silicates with the pyrocatechol is carried out in a solvent medium, especially an alcoholic medium such as methanol, and under an inert atmosphere, in particular a nitrogen atmosphere.

The present invention also relates to the application of the complexes of the formula I to the preparation of organosilanes, these compounds being capable of numerous industrial applications.

Organosilanes are usually prepared by heating elemental silicon with an alkyl or aryl halide in the presence of a copper-based catalyst. This type of reaction has the disadvantage that it most frequently leads to mixtures of various products. Thus, the reaction of silicon with methyl chloride produces a mixture of methylchlorosilanes according to the following reaction scheme:

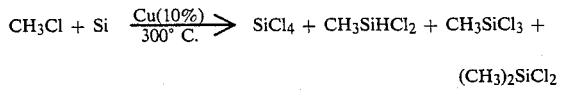

Moreover, mixed organosilanes containing different organic groups cannot be obtained directly by this type of preparative method.

The closest known state of the art can be illustrated by the following two bibliographic references: "Zeitschrift für anorganische und allgemeine Chemie, volume 196", pages 160 et seq. (1931), and "Inorganic Chemistry", volume 12, No. 2, pages 497–498 (1973). The first reference mentions hydrated hexacoordinate silicon complexes and in particular the potassium complex. These hydrated complexes cannot therefore be reacted with an organometallic derivative in view of the presence of the molecules of water of hydration. Furthermore, this document of the prior art does not make the least mention of applications for these complexes. The second reference concerns the preparation of magnesium tris(benzene-1,2-diolato)silicate from a corresponding hdyrated complex. This kind of preparative method involving dehydration is long and difficult to carry out. Again, this second document does not make the least mention of applications for this type of complex.

The present invention in fact makes it possible to overcome the abovementioned disadvantages since it proposes a method for the preparation of organosilanes which no longer has to involve elemental silicon and which also enables a very wide variety of mixed organosilanes to be obtained with excellent yields.

According to the present invention, the process for the preparation of organosilanes of the general formula II:

in which:
R denotes an alkyl, alkenyl, alkynyl, aryl, aralkyl, aralkenyl, aralkynyl or alkylaryl radical in which the aliphatic fragments are linear, branched or cyclic and contain from 1 to 20 carbon atoms, or alternatively a radical SiR''$_3$, in which R'' denotes a radical R, and
R' denotes a hydrogen or halogen atom or alternatively a radical R, comprises reacting an organometallic derivative with a hexacoordinate silicon complex of the general formula I:

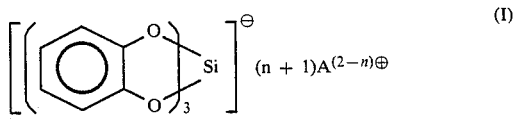

in which:
A represents an alkali metal or alkaline earth metal and
n=0 or 1.

The majority of the organosilanes of the formula II obtained according to the invention are known. They are essentially used in the silicone industry as crosslinking agents and additives for catalyst compositions, or alternatively in the pharmaceutical industry. They have been prepared hitherto from starting materials resulting from the direct synthesis referred to above, by processes requiring a large number of reaction steps.

By contrast, the present invention offers a new route for the synthesis of organosilanes which requires no more than two reaction steps and which enables very pure products to be obtained with excellent yields. This method of preparation also makes it possible rapidly to obtain a very wide variety of mixed organosilanes.

The organometallic derivatives used within the scope of the process forming the subject of the present invention are compounds having at least one organic group joined to a metal atom by a direct carbon-metal bond.

The organic groups present in the organometallic derivatives principally consist of hydrocarbon radicals chosen from the group comprising alkyl, alkenyl, alkynyl, aryl, aralkyl, aralkenyl, aralkynyl or alkylaryl radicals in which the aliphatic fragments are linear, branched or cyclic and contain from 1 to 20 carbon atoms.

Throughout the present description, the aryl radicals and the aromatic fragments of the aralkyl, aralkenyl, aralkynyl and alkylaryl radicals denote phenyl and naphthyl radicals.

Principal examples which may be mentioned of the metals present in such organometallic derivatives are the alkali metals, the alkaline earth metals, the metals of group III, such as aluminum, and the transition metals, such as zinc.

Particular examples which may be mentioned are the alkali metal organometallic derivatives of the general formula III:

R—Alk (III)

in which R has the meaning given above and Alk denotes an alkali metal, such as methylsodium and methyllithium, ethylsodium and ethyllithium, isopropylsodium and isopropyllithium, n-butylsodium and n-butyllithium, vinylsodium and vinyllithium, allylsodium and allyllithium, ethynylsodium and ethynyllithium, propargylsodium and propargyllithium, phenylsodium and phenyllithium and benzylsodium and benzyllithium; the organomagnesium halides of the general formula IV:

R—Mg—X (IV)

in which R has the meaning given above and X denotes a halogen atom, such as methylmagnesium bromide, ethylmagnesium bromide, isopropylmagnesium bromide, tert.-butylmagnesium bromide, vinylmagnesium bromide, allylmagnesium bromide, hexynylmagnesium bromide, phenylmagnesium bromide, benzylmagnesium bromide and phenylethynylmagnesium bromide; the organozinc derivatives of the general formula V:

R₂Zn (V)

in which R has the meaning given above, such as diethylzinc; and the organodimagnesium derivatives of the general formula VI:

in which R''' denotes an alkylene or alkenylene radical containing 3 to 5 carbon atoms and X denotes a halogen atom, such as pentyl-1,5-dimagnesium dichloride, pentyl-1,5-dimagnesium dibromide and but-2(Z)-enyl-1,4-dimagnesium dichloride.

Finally, it is also possible to use other types of organodimetallic derivatives, such as

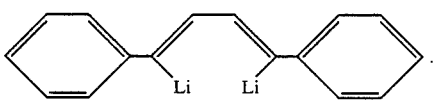

According to another characteristic of the present invention, the reaction of the organometallic derivative with the hexacoordinate silicon complex of the general formula I is carried out by heating under reflux in an anhydrous solvent medium and under an inert atmosphere, for example under a nitrogen atmosphere. The inert solvent medium used is advantageously chosen from aliphatic ethers, such as ethyl ether, dioxane and tetrahydrofuran, or alternatively from hydrocarbons, such as, for example, cyclohexane.

If the hexacoordinate silicon complex of the general formula I is reacted with three equivalents of organometallic derivative, a synthesis intermediate corresponding to the general formula:

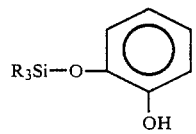

is obtained after hydrolysis, this intermediate itself being capable of reacting with an excess of the starting organometallic derivative to give the organosilane of the formula R₄Si, or with a reducing agent, in particular an inorganic hydride such as lithium aluminum hydride, to give a monohydrogenoorganosilane, or with a hydrohalic acid, such as hydrochloric acid, to give a monochloroorganosilane, or alternatively with a second organometallic derivative corresponding to one of the following general formulae:

R—Alk, R—Mg—X, R₂Zn or R'₃Si—Li in which:
R and R' have the meanings given above with reference to the radical R,
Alk denotes an alkali metal and
X denotes a halogen atom, to give a mixed organosilane.

Advantageously, a monohydrogenoorganosilane can be obtained by reacting lithium aluminum hydride with the intermediate (2-hydroxyphenoxy)silane of the formula:

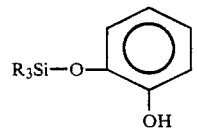

isolated from the reaction medium beforehand. As a variant, the reducing agent can be introduced directly into the reaction medium after the organometallic derivative has completely reacted.

In one variant of the preparative process according to the invention, the reaction of the complex of the formula I with the organometallic derivative, present in excess in the reaction medium, is carried out in the presence of bis(cyclopentadienyl)titanium dichloride to give the corresponding monohydrogenoorganosilane directly.

A number of examples of the preparation of organosilanes obtained according to the various modified versions of the process of the invention are now given below in order to illustrate the process, starting in particular from different types of organometallic derivative, and examples of the preparation of the starting complexes are also given.

EXAMPLE 1

Preparation of sodium tris(benzene-1,2-diolato)silicate

The preparations are carried out under nitrogen in a Schlenk tube with degassed solvents in order to avoid oxidation of the sodium catecholate.

(a) starting from methyl silicate

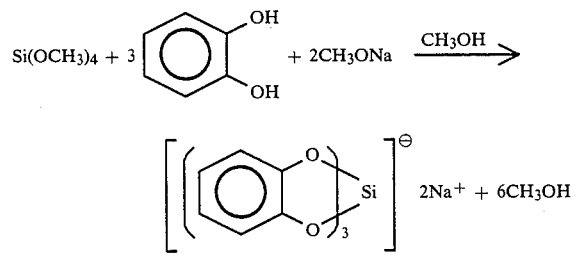

6.4 g (0.278 mol) of sodium are dissolved in 80 ml of methanol. A solution of 22.5 g (0.148 mol) of methyl silicate in 20 ml of methanol is then added, followed by a solution of 47.5 g (0.432 mol) of pyrocatechol in 50 ml of methanol. While the pyrocatechol is being introduced, the reaction mixture becomes milky and then homogeneous. It is heated for 1 hour at 60° C. The methanol is then driven off in vacuo and the complex is washed with ether to remove the excess methyl silicate and pyrocatechol. The complex is filtered off in air and washed twice with ether. It is dried in vacuo at 150° C. for 30 hours to remove all the ether (the ether is strongly absorbed on the complex).

This gives 54.5 g (0.137 mol, 98%) of an amorphous, white air-stable powder which does not melt at 300° C. This complex is soluble in THF, methanol and pyridine and insoluble in the other customary solvents. Spectral characteristics (TMS standard): $^{13}$C NMR (CD$_3$OD) $\delta=151.3$; 118.6; 111.7 ppm. $^{29}$Si NMR (CD$_3$OD) $\delta=-113$ ppm.

(b) starting from silica

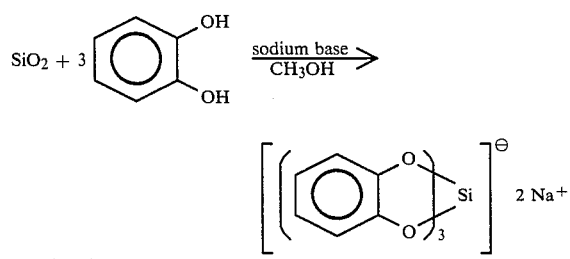

By using the same general conditions as in Example 1a), but replacing the methyl silicate with silica or a silica gel, the same coordination complex is obtained, with a yield of 70%, by heating the reaction mixture for 18 hours at 60° C.

(c) Preparation of calcium tris(benzene-1,2-diolato)silicate from calcium hexafluorosilicate

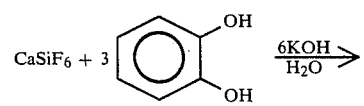

-continued

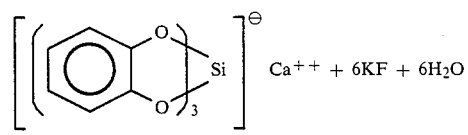

6.8 g (120 mmol) of potassium hydroxide, placed in a Schlenk tube, are dissolved in 40 ml of water. 3.7 g (20 mmol) of CaSiF$_6$ and then 6.6 g (60 mmol) of catechol are added under nitrogen and the mixture is heated at 70° C. for 15 hours. After the water has been driven off, the solid obtained is taken up with 2×100 ml of THF. The mixture obtained is filtered and the filtrate is concentrated in vacuo to give 4.2 g of complex contaminated with catechol. This catechol is removed by washing with ether (2×50 ml). The etherinsoluble complex is isolated by filtration and then dried in vacuo at 120° C. for 6 hours. 2.8 g (35%) of calcium complex are recovered.

EXAMPLE 2

Preparation of lithium tris(benzene-1,2-diolato)silicate

By following the same procedure as in Examples 1a) and 1b), and using lithium methylate, the corresponding lithium comlex is obtained. When starting from methyl silicate, the reaction yield is quantitative (05–100%).

EXAMPLE 3

Preparation of magnesium tris(benzene-1,2-diolato)silicate

By following the same procedure as in Examples 1a) and 1b), and using magnesium methylate, the corresponding magnesium complex is obtained. When starting from methyl silicate, the reaction yield is quantitative (95–100%).

EXAMPLE 4

Preparation of (2-hydroxyphenoxy)silane derivatives (a) General procedure 10 to 20 mmol of the hexacoordinate silicon complex of the general formula I are suspended in 50 to 100 ml of anhydrous ether. 3 equivalents of organometallic derivative are added at room temperature and the reaction mixture is then heated under reflux for 1 to 2 hours. It is subsequently hydrolyzed with 50 ml of a 25% H$_2$SO$_4$ solution and the (2-hydroxyphenoxy)silane derivative is then isolated. The separation is performed as follows. The silicon derivative is extracted three times with ether. The ether solution is washed once with 25 ml of water, twice with 25 ml of 2 N sodium hydroxide solution, twice with 25 ml of water and once with a saturated solution of sodium chloride and dried over magnesium sulfate. After the solvent has been evaporated off, the silicon derivative is purified by distillation or recyrstallization. It is characterized by the IR, NMR and mass spectra.

(b) Preparation of triethyl(2-hydroxyphenoxy)silane

By reacting sodium tris(benzene-1,2-diolato)silicate with 3 equivalents of ethylmagnesium bromide under the above conditions, triethyl(2-hydroxyphenoxy)silane of the formula:

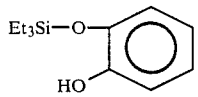

boiling point (1 mm Hg) = 120–123° C.

is obtained with a yield of 72%.

(c) Preparation of [tri(n-butyl)](2-hydroxyphenoxy)-silane

By reacting sodium tris(benzene-1,2-diolato)silicate with 3 equivalents of n-butylmagnesium bromide under the above conditions. [tri(n-butyl)](2-hydroxyphenoxy)silane of the formula:

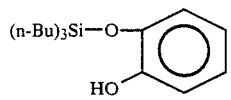

boiling point (0.5 mm Hg) = 140–155° C.

is obtained with a yield of 82%.

(d) Preparation of triallyl(2-hydroxyphenoxy)silane

By reacting sodium tris(benzene-1,2-diolato)silicate with 3 equivalents of allylmagnesium bromide under the above conditions, triallyl(2-hydroxyphenoxy)silane of the formula:

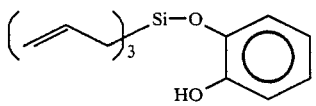

boiling point (0.1 mm Hg) = 106–108° C.

is obtained with a yield of 43%.

EXAMPLE 5

Preparation of monohydrogenoorganosilanes (a) General procedure

The procedure is identical to that described in Example (4a) above. However, instead of being hydrolyzed, the reaction mixture is poured into an excess (n g) of LiAlH$_4$ suspended in ether. After stirring for 3 hours at room temperature, the reaction mixture is hydrolyzed with n ml of water, followed by n ml of 15% sodium hydroxide solution and then 3.n ml of water. The precipitate formed is filtered off and washed with ether. The ether filtrates are washed with water and dried over magnesium sulfate. The solvent is evaporated off and the residue is distilled.

(b) Preparation of tri(n-butyl)silane

By reacting sodium tris(benzene-1,2-diolato)silicate with 3 equivalents of n-butylmagnesium bromide under the above conditions, tri(n-butyl)silane of the formula:

(n-Bu)$_3$Si—H: boiling point (20 mm Hg) = 108°–115° C.

is obtained with a yield of 80%.

(c) Preparation of triethylsilane

By reacting sodium tri(benzene-1,2-diolato)silicate with 3 equivalents of ethylmagnesium bromide under the above conditions, triethylsilane of the formula:

Et$_3$Si—H: boiling point (60 mm Hg) = 40°–45° C.

is obtained with a yield of 60%.

(d) Preparation of tri(isobutyl)silane

By reacting sodium tris(benzene-1,2-diolato)silicate with 3 equivalents of isobutylmagnesium bromide under the above conditions, tri(isobutyl)silane of the formula:

iBu$_3$Si—H: boiling point (15 mm Hg) = 115°–120° C.

is obtained with a yield of 71%.

(e) Preparation of tri(isopropyl)silane

By reacting sodium tris(benzene-1,2-diolato)silicate with 3 equivalents of isopropylmagnesium bromide under the above conditions, tri(isopropyl)silane of the formula:

iPr$_3$Si—H: boiling point (30 mm Hg) = 77°–80° C.

is obtained with a yield of 58%.

(f) Preparation of tribenzylsilane

By reacting sodium tris(benzene-1,2-diolato)silicate with 3 equivalents of benzylmagnesium bromide under the above conditions, tribenzylsilane of the formula:

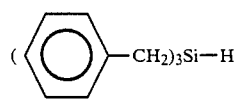

melting point = 90–91° C.

is obtained with a yield of 73%.

EXAMPLE 6

Preparation of chlorosilanes (a) General procedure

The procedure is identical to that described above in Example 4a). However, instead of being hydrolyzed, the reaction mixture is treated with a solution of HCl in anhydrous ether (excess HCl). After the solvent has been evaporated off, the product is distilled.

(b) Preparation of triethylchlorosilane

By reacting sodium tris(benzene-1,2-diolato)silicate with 3 equivalents of ethylmagnesium bromide under the above conditions, triethylchlorosilane of the formula:

Et$_3$Si—Cl: boiling point (95 mm Hg) = 86° C.

is obtained with a yield of 70%.

EXAMPLE 7

Preparation of mixed organosilanes of the formula:
R$_3$Si—R'

(a) General procedure

The procedure is identical to that described above in Example 4(a). However, instead of being hydrolyzed, the reaction mixture is treated with 1 equivalent of reactive organometallic derivative and then heated for 3 hours. The mixture is then hydrolyzed with 50 ml of 25% H$_2$SO$_4$ solution. The silicon compound is isolated as indicated above in Example 4a).

(b) Preparation of triethylallylsilane

By reacting sodium tris(benzene-1,2-diolato)silicate with 3 equivalents of ethylmagnesium bromide and 1 equivalent of allylmagnesium bromide under the above conditions, triethylallylsilane of the formula:

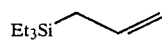

boiling point (35 mm Hg) = 75–80° C.

is obtained with a yield of 70%.

(c) Preparation of triethyl(phenylethynyl)silane

By reacting sodium tris(benzene-1,2-diolato)silicate with 3 eqivalents of ethylmagnesium bromide and 1 equivalent of phenylethynylmagnesium bromide under the above conditions, triethyl(phenylethynyl)silane of the formula:

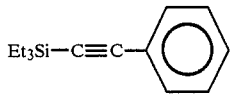

boiling point (25 mm Hg) = 150° C.

is obtained with a yield of 67%.

(d) Preparation of triethylhex-1-ynylsilane

By reacting sodium tris(benzene-1,2-diolato)silicate with 3 equivalents of ethylmagnesium bromide and 1 equivalent of hex-1-ynylmagnesium bromide under the above conditions, triethylhex-1-ynylsilane of the formula:

Et$_3$Si—C↑C(CH$_2$)$_3$CH$_3$: boiling point (760 mm Hg)=185°–189° C.

is obtained with a yield of 49%.

EXAMPLE 8

Preparation of organosilanes of the formula R$_4$Si (a) General procedure

The hexacoordinate silicon complex (10 to 20 mmol) is suspended in 50 to 100 ml of anhydrous ether. 4 equivalents of organometallic derivative are added at room temperature. The reaction mixture is heated under reflux for 1 to 2 hours. It is then hydrolyzed with 50 ml of a 25% H$_2$SO$_4$ solution. The silicon compound is then isolated in the same way as described above in Example 4(a).

(b) Preparation of tetraalylsilane

By reacting sodium tris(benzene-1,2-diolato)silicate with 4 equivalents of allylmagnesium bromide under the above conditions, tetraallylsilane of the formula:

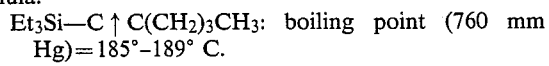

boiling point (23 mm Hg) = 105–112° C.

is obtained with a yield of 68%.

(c) Preparation of tetraphenylsilane

By reacting sodium tris(benzene-1,2-diolato)silicate with 4 equivalents of phenylmagnesium bromide under the above conditions, tetraphenylsilane of the formula:

Ph$_4$Si: melting point=236-237° C. is obtained with a yield of 55%.

(d) Preparation of 6-silaspiro(5,5)undecane

By reacting sodium tris(benzene-1,2-diolato)silicate with 2 equivalents of pentyl-1,5-dimagnesium dichloride under the above conditions, 6-silaspiro(5,5)undecane of the formula

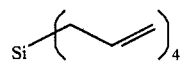

boiling point (25 mm Hg) = 112–120° C.
is obtained with a yield of 40%.

(e) Preparation of tetraphenylethynylsilane

By reacting sodium tris(benzene-1,2-diolato)silicate with 4 equivalents of phenylethynylmagnesium chloride under the above conditions, tetraphenylethynylsilane of the formula:

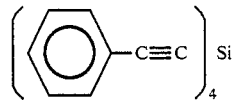

melting point = 193–194° C.

is obtained with a yield of 73%.

(f) Preparation of tetrahex-1-ynylsilane

By reacting sodium tris(benzene-1,2-diolato)silicate with 4 equivalents of hex-1-ynylmagnesium chloride under the above conditions, tetrahex-1-ynylsilane of the formula:

(BuC↑C)$_4$Si: boiling point (0.2 mm Hg)=165°–185° C.

is obtained with a yield of 57%.

EXAMPLE 9

Preparation of Et$_3$Si—SiPh$_3$

The procedure is identical to that described in Example 4a). However, instead of hydrolysis, a solution of Ph$_3$Si$^-$Li$^+$, obtained, for example, according to H. GILMAN and G. D. LICHTENWALTER, J. Amer. Chem. Soc., 1958, 80, 608 (1 equivalent), is added to the reaction medium under nitrogen. After stirring for 2 hours at room temperature, the reaction mixture is filtered. The ether solution is washed several times with water and then dried over MgSO$_4$. The product is recrystallized from 95° alcohol. Yield 85%, melting point=92°–93° C.

EXAMPLE 10

Preparation of triethylsilane in a single step

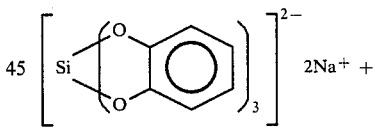

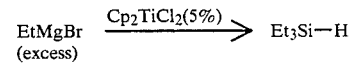

7.96 g of sodium tris(benzene-1,2-diolato)silicate (20 mmol) and 0.251 g of titanium complex (1 mmol) are suspended in 60 ml of anhydrous ether under an argon atmosphere. 100 mmol of ethylmagnesium bromide are added dropwise at room temperature. The reaction mixture is heated under reflux for about 5 hours. It is hydrolyzed with 4 N HCl. The aqueous phase is extracted 3 times with ether. The organic phase is washed with sodium hydroxide solution to remove the pyrocatechol, followed by water until the washings are neutral, and then dried over MgSO$_4$. 1.13 g of Et$_3$Si—H are obtained on distillation (yield=50%). Boiling point (760 mm Hg)=100°–107° C.

What is claimed is:

1. A hexacoordinate silicon complex which corresponds to the general formula I:

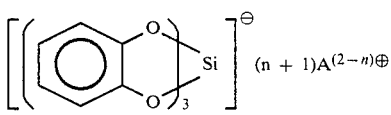  (I)

in which:
A represents an alkali metal or alkaline earth metal except for magnesium, and
n=0 or 1.

2. An application of the complexes of the general formula I:

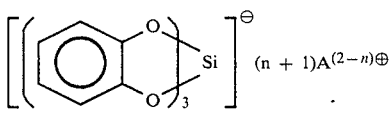  (I)

in which:
A represents an alkali metal or alkaline earth metal and
n=0 or 1, to the preparation of organosilanes of the formula II:

$$R_3Si—R'$$  (II)

in which:
R denotes n alkyl, alkenyl, alkynyl, aryl, aralkyl, aralkenyl, aralkynyl or alkylaryl radical in which the aliphatic fragments are linear, branched or cyclic and contain from 1 to 20 carbon atoms, or alternatively a radical $SiR''_3$, in which R'' denotes a radical R, and
R' denotes a hydrogen or halogen atom or alternatively a radical R, which comprises reacting an organometallic derivative with the abovementioned hexacoordinate silicon complex of the general formula I.

3. The application as claimed in claim 2, wherein the organometallic derivative is an alkali metal organometallic derivative of the general formula III:

$$R—Alk$$  (III)

in which:
R has the meaning given in claim 2 and
Alk denotes an alkali metal.

4. The application as claimed in claim 2, wherein the organometallic derivative is an organomagnesium halide of the general formula IV:

$$R—Mg—X$$  (IV)

in which:
R has the meaning given in claim 2 and
X denotes a halogen atom.

5. The application as claimed in claim 2, wherein the organometallic derivative is an organozinc derivative of the general formula V:

$$R_2Zn$$  (V)

in which:
R has the meaning given in claim 2.

6. The application as claimed in claim 2, wherein the organometallic derivative is an organodimagnesium derivative of the general formula VI:

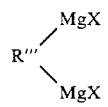  (VI)

in which:
R''' denotes an alkylene or alkenylene radical containing 3 to 5 carbon atoms and
X denotes a halogen atom.

7. The application as claimed in one of claims 2 to 6, wherein the reaction is carried out by heating under reflux in an anhydrous solvent medium and under an inert atmosphere.

8. The application as claimed in one of claims 2 to 6, wherein a reducing agent, in particular an inorganic hydride such as lithium aluminum hydride, is added to the medium, after the organometallic derivative has reacted, to give a hydrogenoorganosilane.

9. The application as claimed in one of claims 2 to 6, wherein the reaction is carried out in the presence of a hydrohalic acid.

10. The application as claimed in one of claims 2 to 6, wherein the reaction is carried out in the presence of a second organometallic derivative of the general formula:

$$R—Alk, R'—Mg—X, R'_2Zn \text{ or } R'_3Si—Li$$

in which R, R', Alk and X have the meanings given above.

11. The application as claimed in one of claims 2 to 9, wherein the reaction is carried out with an excess of organometallic derivatives in the presence of bis(cyclopentadienyl)titanium dichloride.

12. The application as claimed in claim 7, wherein an inorganic hydride reducing agent, is added to the medium, after the organometallic derivative has reacted, to give a hydrogenoorganosilane.

13. The application as claimed in claim 7, wherein the reaction is carried out in the presence of a hydrohalic acid.

14. The application as claimed in claim 8, wherein the reaction is carried out in the presence of a hydrohalic acid.

15. The application as claimed in claim 7, wherein the reaction is carried out in the presence of a second organometallic derivative of the general formula:

$$R—Alk, R'—Mg—X, R'_2Zn \text{ or } R'_3Si—Li$$

in which R, R', Alk and X have the meanings given above.

16. The application as claimed in claim 8, wherein the reaction is carried out in the presence of a second organometallic derivative of the general formula:

$$R-Alk, R'—Mg—X, R'_2Zn \text{ or } R'_3Si—Li$$

in which R, R', Alk and X have the meanings given above.

17. The application as claimed in claim 7, wherein the reaction is carried out with an excess of organometallic derivatives in the presence of bis(cyclopentadienyl)titanium dichloride.

18. The application as claimed in claim 8, wherein the reaction is carried out an excess of organometallic derivatives in the presence of bis(cyclopentadienyl)titanium dichloride.

19. The application as claimed in claim 9, wherein the reaction is carried out with an excess of organometallic derivatives in the presence of bis(cyclopentadienyl)titanium dichloride.

20. The application as claimed in claim 10, wherein the reaction is carried out with an excess of organometallic derivatives in the presence of bis(cyclopentadienyl)titanium dichloride.

* * * * *

UNITED STATES PATENT OFFICE
CERTIFICATE OF CORRECTION

Patent No. 4,841,084

Dated Jun. 20, 1989

Inventor(s) Corriu et al.

It is certified that error appears in the above-identified patent and that said Letters Patent is hereby corrected as shown below:

Column 1, line 10: change --formula I;-- to --formula I:--
Column 2, line 11: delete --hdyrated-- and insert --hydrated--
Column 6, line 29: delete --comlex-- and insert --complex--
Column 6, line 30: delete --(05-100%)-- and insert --(95-100%)--
Column 6, line 62: delete --recyrstallization-- and insert --recrystallization--
Column 7, line 63: delete --tri(benzene-1,2-diolato)-- and insert --tris(benzene-1,2-diolato)--
Column 10, line 31: delete -- 1958, 80, 608-- and insert --1958, 80, 608--
Column 12, line 66: after "out" should read --with--.

Signed and Sealed this

Twenty-fourth Day of April, 1990

Attest:

HARRY F. MANBECK, JR.

Attesting Officer

Commissioner of Patents and Trademarks